US012584151B1

(12) United States Patent
Adamczyk et al.

(10) Patent No.: US 12,584,151 B1
(45) Date of Patent: Mar. 24, 2026

(54) MODIFIED MICROORGANISMS TO INCREASE YIELD OF XYLOSE-DERIVED PRODUCTS

(71) Applicant: National Technology & Engineering Solutions of Sandia, LLC, Albuquerque, NM (US)

(72) Inventors: Paul Alexander Adamczyk, Oakland, CA (US); John Michael Gladden, Martinez, CA (US); Samuel Coradetti, Berkeley, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 788 days.

(21) Appl. No.: 17/880,372

(22) Filed: Aug. 3, 2022

(51) Int. Cl.

| | |
|---|---|
| *C12P 7/58* | (2006.01) |
| *C12N 1/14* | (2006.01) |
| *C12N 1/145* | (2026.01) |
| *C12N 9/04* | (2006.01) |
| *C12N 15/80* | (2006.01) |

(52) U.S. Cl.
CPC ............... *C12P 7/58* (2013.01); *C12N 1/145* (2021.05); *C12N 9/0006* (2013.01); *C12N 15/80* (2013.01); *C12P 2201/00* (2013.01); *C12P 2203/00* (2013.01); *C12Y 101/01307* (2013.01)

(58) Field of Classification Search
None
See application file for complete search history.

(56) References Cited

PUBLICATIONS

Uniprot, Accession No. AOAOK3CLY8, 2022, www.uniprot.org. (Year: 2022).*
Coradetti et al., Functional genomics of lipid metabolism in the oleaginous yeast Rhodosporidium toruloides, eLIFE, Jul. 2018, e32110. (Year: 2018).*
Jagtap et al., Integrating transcriptomic and metabolomic analysis of the oleaginous yeast Rhodosporidium toruloides IFO0880 during growth under different carbon sources, Appl. Microbiol. Biotechnol. 105, 2021, 7411-24. (Year: 2021).*
Toivari et al., Metabolic engineering of *Saccharomyces cerevisiae* for bioconversion of D-xylose to D-xylonate, Metabolic Eng. 14, 2012, 427-36. (Year: 2021).*
Yaegashi et al., Rhodosporidium toruloides: a new platform organism for conversion of lignocellulose into terpene biofuels and bioproducts, Biotechnol. Biofuels 10, 2017, 241. (Year: 2017).*
Wang et al., Improving ethanol yields with deacetylated and two-stage pretreated corn stover and sugarcane bagasse by blending commercial xylose-fermenting and wild type *Saccharomyces* yeast, Bioresource Technol. 282, 2019, 103-109. (Year: 2019).*
Cao, et al., "Metabolic Engineering of *Escherichia coli* for the Production of Xylonate"; PLoS One; Jul. 2013; 8(7): e67305; 8 pages; https://www.researchgate.net/publication/249967597.
Chen, et al., "DMR (deacetylation and mechanical refining) processing of corn stover achieves high monomeric sugar concentrations (230 g L-1) during enzymatic hydrolysis and high ethanol concentrations (>10% v/v) during fermentation without hydrolysate purification or concentration†"; Energy Environ. Sci.; Mar. 1, 2016; 9:1237-1245; www.rsc.org/ees.
Kim, et al., "Multi-Omics Driven Metabolic Network Reconstruction and Analysis of Lignocellulosic Carbon Utilization in Rhodosporidium toruloides"; Frontiers in Bioengineering and Biotechnology; Jan. 8, 2021; 8:612832; 16 pages; www.frontiersin.org.
Otoupal, P. B. et al., "Multiplexed CRISPR-Cas9-Based Genome Editing of Rhodosporidium toruloides," Synthetic Biology (2019) 4(2):e00099-19, 17 pages.
Protzko, et al., "Genomewide and Enzymatic Analysis Reveals Efficient D-Galacturonic Acid Metabolism in the Basidiomycete Yeast Rhodosporidium toruloides"; mSystems; Nov./Dec. 2019; 4(6):e00389-19; 16 pages; mysystems.asm.org.
Zhuang, et al., "Monoterpene production by the carotenogenic yeast Rhodosporidium toruloides"; Microbial Cell Factories (2019) 18:54; 15 pages; https://doi.org/10.1186/s12934-019-1099-8.

* cited by examiner

*Primary Examiner* — Todd M Epstein

(74) *Attorney, Agent, or Firm* — Eschweiler & Potashnik, LLC; Samantha Updegraff

(57) ABSTRACT

Methods and engineered hosts are disclosed that convert a lignocellulosic xylose-containing biomass source into xylonic acid and/or xylonate, which can be further processed into other useful derivatives. In particular, an exemplary engineered Bacidiomycetes, e.g., R. toruloides, host produces/expresses one or more fungal enzymes that convert xylose into xylonic acid/xylonate. Methods of using such hosts to consume pretreated lignocellulosic biomass in combination with certain native promoters and heterologous genes are also described herein.

20 Claims, 9 Drawing Sheets

Specification includes a Sequence Listing.

SEQ ID NO: 1

RT04_9774> UniProt seq ID: A0A0K3CLY8 coding sequence:

```
ATGTCGTCCCAGTCTGTCCCGACCGTCCAGCTGCACAACGGCAAGAGCTTCCCGCTC
CTTGGCTTCGGAACCTGGCAGTCCGCCCCCGGCGAGGTTGGCAATGCCGTTTCTGTC
GCCCTCAAGGCCGGCTACCGCCACCTCGACCTTGCAAAGGTCTACCAGAACCAGAA
GGAGATCGCTCCCGCGATCGCCAACTCGGGCGTGCTCCGTGAGGAGATGTTCATCAC
CTCGAAGCTCTGGAACTCGCAGCACCGTCCGGACCTCGTCGAGCCCGCTCTCGACGA
CACGCTCAAGGAGCTCGGCCTCTCCTACCTCGACCTCTACCTCATCCACTGGCCCGT
CGCATTCCCCGCCGAGGGCGACCCCCACCAGAACCTGTTCCCCAAGGCGAACGACA
ACGAGGTCAAGATTGACGACTCGGTTAGCCTTGTCGACACCTGGAAGGCGATGATC
AAGCTCCTTGACACGGGCAAGGTTAGGTCGATTGGTGTCTCGAACTTCTCGCCTGAG
ATGGTCGATGCTATCACGGAGGCGACCGGCGTCAAGCCCGTCGTCAACCAGATCGA
GCGTCACCCTCACCTCCTCCAGCGCGAGCTGATCGAGCACCACAAGAAGGCAAACA
TCGTCATCACCGCCTACTCCGGTTTCGGCAACAACTCCGAGGGTGTTCCGCTGCTCTT
CCAGCACCCGATCGTCAAGAAGATCGCGGAGAACCACGGCGCGGACGGCGGACAG
GTGTTGATCGCCTGGGGCATGCACGGAGGACACGCGATCATCCCCAAGTCTGTCACC
GAATCTCGCATCCAGTCCAACTTCAAGATTATCCAGCTCGACGAGGCTTCGATCAAG
GAGATTGACTCTATCGGCGAGAAGAACCGCGCCGTTTTAATCTGCCCCGGGCCTAC
GCGCCGTCCTGGCCCATTGACGTCTTCGGAGAGGCCAAAGAGCAGGGTGCGAAGTA
CCAGGTCAAGATCAAGTAA
```

*FIG. 7*

SEQ ID NO. 2

XylB (Uniprot ID: Q9A9Z0)

coding sequence (original WT sequence)

ATGTCCTCAGCCATCTATCCCAGCCTGAAGGGCAAGCGCGTCGTCATCACCGGCGGC
GGCTCGGGCATCGGGGCCGGCCTCACCGCCGGCTTCGCCCGTCAGGGCGCGGAGGT
GATCTTCCTCGACATCGCCGACGAGGACTCCAGGGCTCTTGAGGCCGAGCTGGCCG
GCTCGCCGATCCCGCCGGTCTACAAGCGCTGCGACCTGATGAACCTCGAGGCGATC
AAGGCGGTCTTCGCCGAGATCGGCGACGTCGACGTGCTGGTCAACAACGCCGGCAA
TGACGACCGCCACAAGCTGGCCGACGTGACCGGCGCCTATTGGGACGAGCGGATCA
ACGTCAACCTGCGCCACATGCTGTTCTGCACCCAGGCCGTCGCGCCGGGCATGAAG
AAGCGTGGCGGCGGGGCGGTGATCAACTTCGGTTCGATCAGCTGGCACCTGGGGCT
TGAGGACCTCGTCCTCTACGAAACCGCCAAGGCCGGCATCGAAGGCATGACCCGCG
CGCTGGCCCGGGAGCTGGGTCCCGACGACATCCGCGTCACCTGCGTGGTGCCGGGC
AACGTCAAGACCAAGCGCCAGGAGAAGTGGTACACGCCCGAAGGCGAGGCCCAGA
TCGTGGCGGCCCAATGCCTGAAGGGCCGCATCGTCCCGGAGAACGTCGCCGCGCTG
GTGCTGTTCCTGGCCTCGGATGACGCGTCGCTCTGCACCGGCCACGAATACTGGATC
GACGCCGGCTGGCGTTGA

SEQ ID NO: 3

XylC (Uniprot ID: Q9A9Z1)

coding sequence (original WT sequence)

ATGACCGCTCAAGTCACTTGCGTATGGGATCTGAAGGCCACGTTGGGCGAAGGCCC
GATCTGGCATGGCGACACCCTGTGGTTCGTCGACATCAAGCAGCGTAAAATCCACA
ACTACCACCCCGCCACCGGCGAGCGCTTCAGCTTCGACGCGCCGGATCAGGTGACCT
TCCTCGCGCCGATCGTCGGCGCGACCGGCTTTGTCGTCGGTCTGAAGACCGGGATTC
ACCGCTTCCACCCGGCCACGGGCTTCAGCCTGCTGCTCGAGGTCGAGGACGCGGCG
CTGAACAACCGCCCCAACGACGCCACGGTCGACGCGCAAGGCCGTCTGTGGTTCGG
CACCATGCACGACGGGGAAGAGAACAATAGCGGCTCGCTCTATCGGATGGACCTCA
CCGGCGTCGCCCGGATGGACCGCGACATCTGCATCACCAACGGCCCGTGCGTCTCGC
CCGACGGCAAGACCTTCTACCACACCGACACCCTGGAAAAGACGATCTACGCCTTC
GACCTGGCCGAGGACGGCCTGCTGTCGAACAAGCGCGTCTTCGTGCAGTTCGCCCTG
GGCGACGATGTCTATCCGGACGGTTCGGTCGTCGATTCCGAAGGCTATCTGTGGACC
GCCCTGTGGGGCGGTTTCGGCGCGGTCCGCTTCTCGCCGCAAGGCGACGCCGTGACG
CGCATCGAACTGCCCGCCCCCAACGTCACCAAGCCCTGCTTCGGCGGGCCTGACCTG
AAGACCCTCTATTTCACCACCGCCCGCAAGGGCCTGAGCGACGAGACCCTGGCCCA
GTACCCGCTGGCCGGCGGTGTGTTCGCCGTTCCGGTCGATGTGGCCGGCCAACCCCA
GCATGAGGTCCGCCTTGTCTAA

*FIG. 8*

SEQ ID NO: 4

XylB (Uniprot ID: Q9A9Z0)

coding sequence (codon-optimized for R. toruloides)

ATGTCGTCGGCGATCTACCCGTCGCTCAAGGGCAAGCGCGTCGTCATCACGGGCGG
CGGCTCGGGCATCGGCGCGGGCCTCACGGCGGGCTTCGCGCGCCAGGGCGCGGAGG
TCATCTTCCTCGACATCGCGGACGAGGACTCGCGCGCGCTCGAGGCGGAGCTCGCG
GGCTCGCCGATCCCGCCGGTCTACAAGCGCTGCGACCTCATGAACCTCGAGGCGATC
AAGGCGGTCTTCGCGGAGATCGGCGACGTCGACGTCCTCGTCAACAACGCGGGCAA
CGACGACCGCCACAAGCTCGCGGACGTCACGGGCGCGTACTGGGACGAGCGCATCA
ACGTCAACCTCCGCCACATGCTCTTCTGCACGCAGGCGGTCGCGCCGGGCATGAAG
AAGCGCGGCGGCGGCGCGGTCATCAACTTCGGCTCGATCTCGTGGCACCTCGGCCTC
GAGGACCTCGTCCTCTACGAGACGGCGAAGGCGGGCATCGAGGGCATGACGCGCGC
GCTCGCGCGCGAGCTCGGCCCGGACGACATCCGCGTCACGTGCGTCGTCCCGGGCA
ACGTCAAGACGAAGCGCCAGGAGAAGTGGTACACGCCGGAGGGCGAGGCGCAGAT
CGTCGCGGCGCAGTGCCTCAAGGGCCGCATCGTCCCGGAGAACGTCGCGGCGCTCG
TCCTCTTCCTCGCGTCGGACGACGCGTCGCTCTGCACGGGCCACGAGTACTGGATCG
ACGCGGGCTGGCGCTGA

SEQ ID NO: 5

XylC (Uniprot ID: Q9A9Z1)

coding sequence (codon-optimized for R. toruloides)

ATGACGGCGCAGGTCACGTGCGTCTGGGACCTCAAGGCGACGCTCGGCGAGGGCCC
GATCTGGCACGGCGACACGCTCTGGTTCGTCGACATCAAGCAGCGCAAGATCCACA
ACTACCACCCGGCGACGGGCGAGCGCTTCTCGTTCGACGCGCCGGACCAGGTCACG
TTCCTCGCGCCGATCGTCGGCGCGACGGGCTTCGTCGTCGGCCTCAAGACGGGCATC
CACCGCTTCCACCCGGCGACGGGCTTCTCGCTCCTCGAGGTCGAGGACGCGGCG
CTCAACAACCGCCCGAACGACGCGACGGTCGACGCGCAGGGCCGCCTCTGGTTCGG
CACGATGCACGACGGCGAGGAGAACAACTCGGGCTCGCTCTACCGCATGGACCTCA
CGGGCGTCGCGCGCATGGACCGCGACATCTGCATCACGAACGGCCCGTGCGTCTCG
CCGGACGGCAAGACGTTCTACCACACGGACACGCTCGAGAAGACGATCTACGCGTT
CGACCTCGCGGAGGACGGCCTCCTCTCGAACAAGCGCGTCTTCGTCCAGTTCGCGCT
CGGCGACGACGTCTACCCGGACGGCTCGGTCGTCGACTCGGAGGGCTACCTCTGGA
CGGCGCTCTGGGGCGGCTTCGGCGCGGTCCGCTTCTCGCCGCAGGGCGACGCGGTC
ACGCGCATCGAGCTCCCGGCGCCGAACGTCACGAAGCCGTGCTTCGGCGGCCCGGA
CCTCAAGACGCTCTACTTCACGACGGCGCGCAAGGGCCTCTCGGACGAGACGCTCG
CGCAGTACCCGCTCGCGGGCGGCGTCTTCGCGGTCCCGGTCGACGTCGCGGGCCAG
CCGCAGCACGAGGTCCGCCTCGTCTGA

*FIG. 9*

SEQ ID NO: 6

PGAPDH>

TCCTTCCGTTCGTTGCAAGGATCGTCTGCATGTTTCGCTTCTCTCAATGACACAACCT
GGAGAGCGCTCCCGTCAGCGAGAATCGAGGACATTCCGCAGCTCGTGAGCAAGCGG
AGGTGCGAGGCTCCCTCGAAAGCTGCGCCTCTTCAGACGGCTTGTTCTCTCCTGCTC
TGGTGGGCTGGCCTGACATGTAATGTGCTCCGCCGCAAGTCCGTCGTCGGTCTCAAT
TCGACGTTGAAAGGGCATAGCGCAAGGAAGAACCCTCTGCGGACATGCAGAATTAC
TGGCTCGCCTGCTCCTTCGTCTACTGGAATAAGTCCTGTCTCGTTAAAGCCCCAACGT
CGTTTTTCGACGTTTGTAAGGCGCAAGAGGTGCTATGGGCTACGCAGGAAGCTGAG
AGGACATAGAAGTCGGGGGAGGAACGGCGCAGAGCGGCAGTTGCGGAAGCATGAG
GAAAGCGAGACGGTCCAGCATCTGCAGCGCCAATCCGCAATCTCCTGGTTGAGCCT
GCACCGGAAGCGTCGGAACAGTATGCGCAGAGTCGAACGCAAGTAAGAAAGACGC
ACCCTCACACTCGCTTACTTCGAGCCATACAACGGATCAAAGCTGCGCGTATCTCGG
CTTGTAAGGGCCGGAAAGCAACCTCGGAGATGGACACGTCACATCACCAACTTATC
GATCTCGGCCGTCGACGTCGCAGAGAGGGCGAGAGAAGCGGTGAAGGAGGGAAAC
AACCCCTCGAGAGCATGATCCGACCGAATCTGCAGCGCAGGAAGCCGTTACAAGCC
CGCCTCGAGCGCAGGTCGGGTCCAGCCGGGGGACGAAACGCGCGAGGCTGATTCGT
GAGCGAAGGAAGCCGCATCGACAAGTTCGCTCCCCTTTGCCCTCTTTCCCATCACCC
GTTCTCGCCTTACCCGCTCAGAACAACACCAGATCACTCACA

SEQ ID NO: 7

PTEF1>

CGCGAAGCGGTAGAAGCAATGAAGCGAGGCGAGAGCGAGAGAGGCAGGGCTTCAG
CCATGTCCAGCTGATCGGCTGTAACGTCGCGCCGGGCCAGTCTGTTGAATTTGTTGC
GTCGCCTGAGCGTAATAGAAGTGCAGTAGTCTACTCCGCATGCCGAGAACGTCGAA
GAGCGCGAAGTAGGGAGTCGAGGGAAGCGAGGGTGGCAAACACAGCAACGACAAG
CGGTTCCGCTTCGCTCAAAAGCTCGTTGACGTTGTTTTGACGTTTTGAAGACAGTAC
AACAGCAGCAAGAGGCGTGCGAAGCGTTGGTGGCGAGAGCAGCGACAAGGAGGGA
GGAATGAGGGAGTGGTGGCGAGGGCTCGCAAACGGGCGTACGCCTCGAATGGAGA
CGTGCGAGTCGTTCTTCGACGTCCGAGGGATGCCGAGCGCCGAGACGGAGCACGCA
ACGAGCGAGAGGAGAGCAGCCGCGCAAGGTGATTCGAGTGGCGCAAGCGGAGGAC
GACGAGGAGACGGACGAGGGAGGAGGAGGGATGGCGAGCGAGCATCGGACGGCGG
GGCGCGAGAGACGGCGTGAGGAGCCGGGTGTGGAGAGTTTGAGGAGGCGCGGGAT
GCGAAGTGGCTGGGTGTGCGGAGTGAGCGGTGGCAAAGAGCGCACTTAGAGTCTAG
AGCGAGGCAGTAGTAGTAGAGCTGTATGAATGAATACAAAGTGTGAATACAACAGT
TTGTAATGCGATTCTGAGCTTGGACGTGTGCGCGCGAGAGGGCGACTTGCAAGCCA
GCGCCCGCTCGCTCTTCTTCCTTCTGCACCTCGCGTCAACCCTCGCATCTCACACCTA
CACTCGCATTCAAAGTGCGTACACTCTCCCACGACACACGGGGACGGCGCACACCA
CCGCGCGTCGCTTGAACGGCGTCGCCACTTCGAGCCGTCACTGACTTCGTCCTCGTC
CTCCCTCCTCTACTCTCTTGTACTGTACTGTGTACTGGGGGGGATAG

*FIG. 10*

SEQUENCE LISTING

```
Sequence total quantity: 12
SEQ ID NO: 1            moltype = DNA   length = 981
FEATURE                 Location/Qualifiers
misc_feature            1..981
                        note = Synthetic: RT04_9774 UniProt ID: A0A0K3CLY8; coding
                        sequence;derived from R. toruloides
source                  1..981
                        mol_type = other DNA
                        organism = synthetic construct
SEQUENCE: 1
atgtcgtccc agtctgtccc gaccgtccag ctgcacaacg gcaagagctt cccgctcctt   60
ggcttcggaa cctggcagtc cgcccccggc gaggttggca atgccgtttc tgtcgccctc  120
aaggccggct accgccacct cgaccttgca aaggtctacc agaaccagaa ggagatcgct  180
cccgcgatcg ccaactcggg cgtgctccgt gaggagatgt tcatcacctc gaagctctgg  240
aactcgcagc accgtccgga cctcgtcgag cccgctctcg acgacacgct caaggagctc  300
ggcctctcct acctcgacct ctacctcatc cactggcccg tcgcattccc cgccgagggc  360
gaccccacc agaacctgtt ccccaaggcg aacgacaacg aggtcaagat tgacgactcg  420
gttagccttg tcgacacctg gaaggcgatg atcaagctcc ttgacacggg caaggttagg  480
tcgattggtg tctcgaactt ctcgcctgag atggtcgatg ctatcacgga ggcgaccggc  540
gtcaagcccg tcgtcaacca gatcgagcgt caccctcacc tcctccagcg cgagctgatc  600
gagcaccaca agaaggcaaa catcgtcatc accgcctact ccggtttcgg caacaactcc  660
gagggtgttc cgctgctctt ccagcacccg atcgtcaaga agatcgcgga gaaccacggc  720
gcggacggcg gacaggtgtt gatcgcctgg ggcatgcacg gaggacacgc gatcatcccc  780
aagtctgtca ccgaatctcg catccagtcc aacttcaaga ttatccagct cgacgaggct  840
tcgatcaagg agattgactc tatcggcgag aaagaaccgc gccgttttaa tctgccccgg  900
```

```
gcctacgcgc cgtcctggcc cattgacgtc ttcggagagg ccaaagagca gggtgcgaag  960
taccaggtca agatcaagta a                                             981

SEQ ID NO: 2          moltype = DNA  length = 747
FEATURE               Location/Qualifiers
misc_feature          1..747
                      note = XylB (Uniprot ID: Q9A9Z0); coding sequence (original
                      WT sequence)
source                1..747
                      mol_type = genomic DNA
                      organism = Caulobacter crescentus
SEQUENCE: 2
atgtcctcag ccatctatcc cagcctgaag ggcaagcgcg tcgtcatcac cggcggcggc  60
tcgggcatcg gggccggcct caccgccggc ttcgcccgtc agggcgcgga ggtgatcttc  120
ctcgacatcg ccgacgagga ctccagggct cttgaggccg agctggccgg ctcgccgatc  180
ccgccggtct acaagcgctg cgacctgatg aacctcgagg cgatcaaggc ggtcttcgcc  240
gagatcggcg acgtcgacgt gctggtcaac aacgccggca atgacgaccg ccacaagctg  300
gccgacgtga ccggcgccta ttgggacgag cggatcaacg tcaacctgcg ccacatgctg  360
ttctgcaccc aggccgtcgc gccgggcatg aagaagcgtg gcggcggggc ggtgatcaac  420
ttcggttcga tcagctggca cctggggctt gaggacctcg tcctctacga aaccgccaag  480
gccggcatcg aaggcatgac ccgcgcgctg gcccgggagc tgggtcccga cgacatccgc  540
gtcacctgcg tggtgccggg caacgtcaag accaagcgcc aggagaagtg gtacacgccc  600
gaaggcgagg cccagatcgt ggcggcccaa tgcctgaagg gccgcatcgt cccggagaac  660
gtcgccgcgc tggtgctgtt cctggcctcg gatgacgcgt cgctctgcac cggccacgaa  720
tactggatcg acgccggctg gcgttga                                      747

SEQ ID NO: 3          moltype = DNA  length = 870
FEATURE               Location/Qualifiers
misc_feature          1..870
                      note = XylC (Uniprot ID: Q9A9Z1); coding sequence (original
                      WT sequence)
source                1..870
                      mol_type = genomic DNA
                      organism = Caulobacter crescentus
SEQUENCE: 3
atgaccgctc aagtcacttg cgtatgggat ctgaaggcca cgttgggcga aggcccgatc  60
tggcatggcg acaccctgtg gttcgtcgac atcaagcagc gtaaaatcca caactaccac  120
cccgccaccg gcgagcgctt cagcttcgac gcgccggatc aggtgacctt cctcgcgccg  180
atcgtcgggc gacccggctt tgtcgtcggt ctgaagaccg ggattcaccg cttccaccg  240
gccacgggct tcagcctgct gctcgaggtc gaggacgcgg cgctgaacaa ccgcccaac  300
gacgccacgg tcgacgcgca aggccgtctg tggttcggca ccatgcacga cggggaagag  360
aacaatagcg gctcgctcta tcggatggac ctcaccggcg tcgcccggat ggaccgcgac  420
atctgcatca ccaacggccc gtgcgtctcg cccgacggca agaccttcta ccacaccgac  480
accctggaaa agacgatcta cgccttcgac ctggccgagg acggcctgct gtcgaacaag  540
cgcgtcttcg tgcagttcgc cctgggcgac gatgtctatc cggacggttc ggtcgtcgat  600
tccgaaggct atctgtggac cgccctgtgg ggcggtttcg gcgcggtccg cttctcgccg  660
caaggcgacg ccgtgacgcg catcgaactg cccgccccca acgtcaccaa gccctgcttc  720
ggcgggcctg acctgaagac cctctatttc accaccgccc gcaagggcct gagcgacgag  780
acctggcccc agtaccgct ggcggcggt gtgttcgccg ttcggtcga tgtggccggc  840
caaccccagc atgaggtccg ccttgtctaa                                   870

SEQ ID NO: 4          moltype = DNA  length = 747
FEATURE               Location/Qualifiers
misc_feature          1..747
                      note = Synthetic: XylB (Uniprot ID: Q9A9Z0); coding
                      sequence(codon-optimized for R. toruloides)
source                1..747
                      mol_type = other DNA
                      organism = synthetic construct
SEQUENCE: 4
atgtcgtcgg cgatctaccc gtcgctcaag ggcaagcgcg tcgtcatcac gggcggcggc  60
tcgggcatcg gcgcgggcct cacggcgggc ttcgcgcgcc agggcgcgga ggtcatcttc  120
ctcgacatcg cggacgagga ctcgcgcgcg ctcgaggcgg agctcgcggg ctcgccgatc  180
ccgccggtct acaagcgctg cgacctcatg aacctcgagg cgatcaaggc ggtcttcgca  240
gagatcggcg acgtcgacgt cctcgtcaac aacgcgggca cgacgaccg ccacaagctc  300
gcggacgtca cgggcgcgta ctgggacgag cgcatcaacg tcaacctccg ccacatgctc  360
ttctgcacgc aggcggtcgc gccgggcatg aagaagcgcg cgggcggcgc ggtcatcaac  420
ttcggctcga tctcgtggca cctcggcctc gaggacctcg tcctctacga gacggcgaag  480
gcgggcatcg agggcatgac gcgcgcgctc gcgcgcgagc tcggcccgga cgacatccgc  540
gtcacgtgcg tcgtcccggg caacgtcaag acgaagcgcc aggagaagtg gtacacgccg  600
gagggcgagg cgcagatcgt cgcggcgcag tgcctcaagg gccgcatcgt cccggagaac  660
gtcgcggcgc tcgtcctctt cctcgcgtcg gacgacgcgt cgctctgcac gggccacgag  720
tactggatcg acgcgggctg cgcgtga                                      747

SEQ ID NO: 5          moltype = DNA  length = 870
FEATURE               Location/Qualifiers
misc_feature          1..870
                      note = Synthetic: XylC (Uniprot ID: Q9A9Z1); coding
                      sequence(codon-optimized for R. toruloides)
```

-continued

```
source                  1..870
                        mol_type = other DNA
                        organism = synthetic construct
SEQUENCE: 5
atgacggcgc aggtcacgtg cgtctgggac ctcaaggcga cgctcggcga gggcccgatc    60
tggcacggcg acacgctctg gttcgtcgac atcaagcagc gcaagatcca caactaccac   120
ccggcgacgg gcgagcgctt ctcgttcgac gcgccggacc aggtcacgtt cctcgcgccg   180
atcgtcggcg cgacgggctt cgtcgtcggc ctcaagacgg gcatccaccg cttccacccg   240
gcgacgggct tctcgctcct cctcgaggtc gaggacgcgg cgctcaacaa ccgcccgaac   300
gacgcgacgg tcgacgcgca gggccgcctc tggttcggca cgatgcacga cggcgaggag   360
aacaactcgg gctcgctcta ccgcatggac ctcacgggcg tcgcgcgcat ggaccgcgac   420
atctgcatca cgaacggccc gtgcgtctcg ccggacggca agacgttcta ccacacggac   480
acgctcgaga agacgatcta cgcgttcgac ctcgcggagg acggcctcct ctcgaacaag   540
cgcgtcttcg tccagttcgc gctcgagcaa gacgtctacc cggacggctc ggtcgtcgac   600
tcggagggct acctctggac ggcgctctgg ggcggcttcg gcgcggtccg cttctcgccg   660
cagggcgacg cggtcacgcg catcgagctc ccggcgccga acgtcacgaa gccgtgcttc   720
ggcggccgg acctcaagac gctctacttc acgacggcgc gcaagggcct ctcggacgag   780
acgctcgcgc agtacccgct cgcggggcggc gtcttcgcgg tcccggtcga cgtcgcgggc   840
cagccgcagc acgaggtccg cctcgtctga                                    870

SEQ ID NO: 6             moltype = DNA  length = 943
FEATURE                 Location/Qualifiers
misc_feature            1..943
                        note = Synthetic: PGAPDH
source                  1..943
                        mol_type = other DNA
                        organism = synthetic construct
SEQUENCE: 6
tccttccgtt cgttgcaagg atcgtctgca tgtttcgctt ctctcaatga cacaacctgg    60
agagcgctcc cgtcagcgag aatcgaggac attccgcagc tcgtgagcaa gcggaggtgc   120
gaggctccct cgaaagctgc gcctcttcag acggcttgtt ctctcctgct ctggtgggct   180
ggcctgacat gtaatgtgct ccgccgcaag tccgtcgtcg gtctcaattc gacgttgaaa   240
gggcatagcg caaggaagaa ccctctgcgg acatgcagaa ttactggctc gcctgctcct   300
tcgtctactg gaataagtcc tgtctcgtta aagccccaac gtcgtttttc gacgtttgta   360
aggcgcaaga ggtgctatgg gctacgcagg aagctgagag gacatagaag tcgggggagg   420
aacggcgcag agcggcagtt gcggaagcat gaggaaagcg agacggtcca gcatctgcag   480
cgccaatccg caatctcctg gttgagcctg caccggaagc gtcggaacag tatgcgcaga   540
gtcgaacgca agtaagaaag acgcaccctc acactcgctt acttcgagcc atacaacgga   600
tcaaagctgc gcgtatctcg gcttgtaagg gccggaaagc aacctcggag atggacacgt   660
cacatcacca acttatcgat ctcggccgtc gacgtcgcag agagggcgag agaagcggtg   720
aaggagggaa acaacccctc gagagcatga tccgaccgaa tctgcagcgc aggaagccgt   780
tacaagcccg cctcgagcgc aggtcgggtc cagccggggg acgaaacgcg cgaggctgat   840
tcgtgagcga aggaagccgc atcgacaagt tcgctcccct ttgccctctt tcccatcacc   900
cgttctcgcc ttacccgctc agaacaacac cagatcactc aca                     943

SEQ ID NO: 7             moltype = DNA  length = 997
FEATURE                 Location/Qualifiers
misc_feature            1..997
                        note = Synthetic:PTEF1
source                  1..997
                        mol_type = other DNA
                        organism = synthetic construct
SEQUENCE: 7
cgcgaagcgg tagaagcaat gaagcgaggc gagagcgaga gaggcagggc ttcagccatg    60
tccagctgat cggctgtaac gtcgcagccgg gccagtctgt tgaatttgtt gcgtcgcctg   120
agcgtaatag aagtgcagta gtctactccg catgccgaga acgtcgaaga gcgcgaagta   180
gggagtcgag ggaagcgagg gtggcaaaca cagcaacgac aagcggttcc gcttcgctca   240
aaaagctcgtt gacgttgttt tgacgttttg aagacagtac aacagcagca agaggcgtgc   300
gaagcgttgg tggcgagagc agcgacaagg agggaggaat gagggagtgg tggcgagggc   360
tcgcaaacgg gcgtacgcct cgaatggaga cgtgcgagtc gttcttcgac gtccgaggga   420
tgccgagcgc cgagacggag cacgcaacga gcgagaggag agcagccgcg caaggtgatt   480
cgagtggcgc aagcggagga cgacgaggag acgacgagg gaggaggagg gatggcgagc   540
gagcatcgga cggcgggcg cgagagacgg cgtgaggagc cgggtgtgga gagtttgagg   600
aggcgcggga tgcgaagtgg ctgggtgtgc ggagtgacgc gtggcaaaga gcgcacttag   660
agtctagagc gaggcagtag tagtagagct gtatgaatga atacaaagtg tgaatacaac   720
agtttgtaat gcgattctga gcttggacgt gtgcgcgcga gagggcgact tgcaagccag   780
cgcccgctcg ctcttcttcc ttctgcacct cgcgtcaacc ctcgcatctc acacctacac   840
tcgcattcaa agtgcgtaca ctctcccacg acacacgggg acggcgcaca ccaccgcgcg   900
tcgcttgaac ggcgtcgcca cttcgagccg tcactgactt cgtcctcgtc ctccctcctc   960
tactctcttg tactgtactg tgtactgggg gggatag                            997

SEQ ID NO: 8             moltype = DNA  length = 60
FEATURE                 Location/Qualifiers
misc_feature            1..60
                        note = Synthetic: 9774.LHF.F
source                  1..60
                        mol_type = other DNA
                        organism = synthetic construct
SEQUENCE: 8
```

-continued

```
cccgctcgct cgctgaaaaa gtgcgctggg gctgcttgat cgatgtcgct cgtcttgttt  60

SEQ ID NO: 9          moltype = DNA  length = 60
FEATURE               Location/Qualifiers
misc_feature          1..60
                      note = Synthetic: 9774.RHF.R
source                1..60
                      mol_type = other DNA
                      organism = synthetic construct
SEQUENCE: 9
tctcgacggg cctctcctcg ctctcacgtc tcccaaactc gcccagagcc gacggagaac  60

SEQ ID NO: 10         moltype = DNA  length = 30
FEATURE               Location/Qualifiers
misc_feature          1..30
                      note = Synthetic: LHF.162B.F2
source                1..30
                      mol_type = other DNA
                      organism = synthetic construct
SEQUENCE: 10
tgagcgtgtc gagcttcgcg acgttcggta                                    30

SEQ ID NO: 11         moltype = DNA  length = 27
FEATURE               Location/Qualifiers
misc_feature          1..27
                      note = Synthetic: LHF.162B.R2
source                1..27
                      mol_type = other DNA
                      organism = synthetic construct
SEQUENCE: 11
agcgggtcag tgagcgggtc tggtggg                                       27

SEQ ID NO: 12         moltype = DNA  length = 29
FEATURE               Location/Qualifiers
misc_feature          1..29
                      note = Synthetic: LHF2.162B.R2
source                1..29
                      mol_type = other DNA
                      organism = synthetic construct
SEQUENCE: 12
tcgcgcgccc acttgtagcc gtagaggtc                                     29
```

MODIFIED MICROORGANISMS TO INCREASE YIELD OF XYLOSE-DERIVED PRODUCTS

STATEMENT OF GOVERNMENT INTEREST

This invention was made with Government support under Contract No. DE-NA0003525 awarded by the United States Department of Energy/National Nuclear Security Administration. The U.S. Government has certain rights in the invention.

REFERENCE TO A SEQUENCE LISTING APPENDIX

A sequence listing appendix including XML file in accordance with WIPO ST.26 accompanies this application. The appendix includes a file named "SD-15938," created on Jul. 13, 2022 (size of 21.7 kilobytes), which is hereby incorporated by reference in its entirety.

FIELD OF THE INVENTION

The present disclosure relates to methods and engineered microbial hosts useful for treating biomass hydrolysates. In particular, the disclosure relates to a modified Rhodosporidum yeast for improving production of xylonic acid from a xylose-containing biomass source.

BACKGROUND OF THE INVENTION

Derivatives of xylose, such as xylonic acid, find use in pharmaceuticals, food, solvents, dyes, concrete and other products. Xylonic acid is a precursor to a plethora of downstream products such as ethylene glycol, 1,2,4-butanetriol, 1,4-butanediol, and glycolic acid, each of which have substantial industrial demand.

There is a need to valorize or convert lignocellulosic biomass into valuable products. In particular, biomass sources from corn production, such as corn stover or distillers' dried grains (DDGs), make up a large segment of unused biomass in the United States. Production of DDGS has dramatically increased in the last few decades. Despite potential utility for this product for animal feed blending, market adoption of the feedstock has been limited. Such co-products, as well as other biomass products, can contain high value components that are difficult to recover and isolate. Accordingly, there is a need for methods and tools to facilitate such isolation in an effective and/or efficient manner.

Microbial hosts may be used for converting xylose-rich biomass sources into other products. For example, Xylitol, a sugar substitute, can be produced by fermentation of such biomass. Certain wild-type hosts, such as Rhodosporidium, e.g., R. toruloides have a natural pathway that catabolizes xylose toward cellular growth. This pathway is desirable for some products.

SUMMARY

The present disclosure relates to methods and engineered hosts to convert a lignocellulosic xylose-containing biomass source into xylonic acid. In particular, we describe an exemplary engineered Rhodosporidum, e.g., Rhodosporidium toruloides, host that produces/expresses one or more fungal enzymes that can convert pretreated, xylose-containing lignocellulosic biomass into xylonic acid/xylonate.

Methods of using such hosts on pretreated lignocellulosic biomass are also described herein.

In an embodiment, a method of making a xylose-derived product via a fermentation broth, comprises: combining an energy source comprising xylose and an engineered host, the engineered host being derived from a Basidiomycete organism having a gene with 70% sequence identity to RT04_9774 in its genome, and the engineered host having the gene with 70% sequence identity to RT04_9774 deleted from its genome.

In an embodiment, an engineered organism comprises an engineered host derived from a Basidiomycete organism having a gene with 70% sequence identity to RT04_9774 in its genome, the engineered host being exclusive of the gene with 70% sequence identity to RT04_9774.

In an embodiment, a fermented broth composition comprises: an energy source comprising xylose and an engineered host, the engineered host being derived from a Basidiomycete organism having a gene with 70% sequence identity to RT04_9774 in its genome, and the engineered host having the gene with 70% sequence identity to RT04_9774 deleted from its genome.

Definitions

As used herein, the term "about" means +/−10% of any recited value. As used herein, this term modifies any recited value, range of values, or endpoints of one or more ranges.

In any of the embodiments herein, a contiguous fragment can include at least 5, 10, 11, 12, 13, 14, 15, 16, 17, 18, 19, 20, 21, 22, 23, 24, or 25 contiguous nucleotides from a full-length nucleic acid sequence. In some embodiments, the contiguous fragment includes of from about 5 to about 100 nucleotides (e.g., from 5 to 10, 5 to 25, 5 to 50, 5 to 75, 5 to 100, 10 to 25, 10 to 50, 10 to 75, 10 to 100, 20 to 25, 20 to 50, 20 to 75, 20 to 100, 25 to 50, 25 to 75, 25 to 100, 50 to 75, 50 to 100, or 75 to 100 nucleotides).

In any of the embodiments herein, a contiguous fragment can include at least 5, 6, 7, 8, 9, 10, 11, 12, 13, 14, 15, 16, 17, 18, 19,20,25,50,75,90, 100, 150,200,250,300, or350 contiguous amino acids from a full-length amino acid sequence. In some embodiments, the contiguous fragment includes of from about 5 to about 350 amino acids (e.g., from 5 to 10, 5 to 25, 5 to 50, 5 to 75, 5 to 100, 5 to 150, 5 to 200, 5 to 250, 5 to 300, 10 to 25, 10 to 50, 10 to 75, 10 to 100, 10 to 150, 10 to 200, 10 to 250, 10 to 300, 10 to 350, 20 to 25, 20 to 50, 20 to 75, 20 to 100, 20 to 150, 20 to 200, 20 to 250, 20 to 300, 20 to 350, 25 to 50, 25 to 75, 25 to 100, 25 to 150, 25 to 200, 25 to 250, 25 to 300, 25 to 350, 50 to 75, 50 to 100, 50 to 150, 50 to 200, 50 to 250, 50 to 300, 50 to 350, 75 to 100, 75 to 150, 75 to 200, 75 to 250, 75 to 300, and 75 to 350 amino acids).

In any embodiment herein, at least 70% sequence identity to a reference sequence can include at least 73%, 80%, 90%, 95%, 96%, 97%, 98%, or 99% sequence identity to the reference sequence (e.g., the reference nucleic acid sequence or the reference amino acid sequence). Sequence identity calculation is based on the number of amino acids that differ from the total number of amino acids on a protein level. An example of a software package for calculating sequence identity is BLAST, which is applicable to the present invention by entering a string corresponding to the sequences herein.

The terms "polynucleotide" and "nucleic acid," used interchangeably herein, refer to a polymeric form of nucleotides of any length, either ribonucleotides or deoxyribonucleotides. Thus, this term includes, but is not limited to, single-stranded (e.g., sense or antisense), double-stranded, or multi-stranded ribonucleic acids (RNAs), deoxyribonucleic acids (DNAs), threose nucleic acids (TNAs), glycol nucleic acids (GNAs), peptide nucleic acids (PNAs), locked nucleic acids (LNAs), or hybrids thereof, genomic DNA, cDNA, DNA-RNA hybrids, or a polymer comprising purine and pyrimidine bases or other natural, chemically or biochemically modified, non-natural, or derivatized nucleotide bases. Polynucleotides can have any useful two-dimensional or three-dimensional structure or motif, such as regions including one or more duplex, triplex, quadruplex, hairpin, and/or pseudoknot structures or motifs. For any nucleic acid sequence described herein, uracil (U) may be thymine (T), and T may be U.

The term "modified," as used in reference to nucleic acids, means a nucleic acid sequence including one or more modifications to the nucleobase, nucleoside, nucleotide, phosphate group, sugar group, and/or internucleoside linkage (e.g., phosphodiester backbone, linking phosphate, or a phosphodiester linkage).

A nucleoside modification may include, but is not limited to, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, $N^4$-acetylcytidine, 5-formylcytidine, $N^4$-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, $N^6$-methyladenosine, $N^6$-isopentenyladenosine, $N^6$-(cis-hydroxy-isopentenyl)adenosine, 2-methylthio-$N^6$-(cis-hydroxyisopentenyl) adenosine, $N^6$-glycinylcarbamoyladenosine, $N^6$-threonylcarbamoyladenosine, 2-methylthio-$N^6$-threonyl carbamoyladenosine, $N^6,N^6$-dimethyladenosine, 7-methyl-adenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, $N^2$-methylguanosine, $N^2,N^2$-dimethylguanosine, 8-oxo-guanosine, 7-methyl-8-oxo-guanosine, 1-methyl-6-thio-guanosine, $N^2$-methyl-6-thio-guanosine, and $N^2,N^2$-dimethyl-6-thio-guanosine, and combinations thereof.

A sugar modification may include, but is not limited to, a locked nucleic acid (LNA, in which the 2'-hydroxyl is connected by a $C_{1-6}$ alkylene (e.g., a multivalent (e.g., bivalent, trivalent, tetravalent, etc.) form of an alkyl group) or $C_{1-6}$ heteroalkylene (e.g., a divalent form of an alkylene group containing one, two, three, or four non carbon heteroatoms (e.g., independently selected from the group consisting of nitrogen, oxygen, phosphorous, sulfur, or halo) bridge to the 4'-carbon of the same ribose sugar), replacement of the oxygen in ribose (e.g., with S, Se, or alkylene, such as methylene or ethylene), addition of a double bond (e.g., to replace ribose with cyclopentenyl or cyclohexenyl), ring contraction of ribose (e.g., to form a 4-membered ring of cyclobutane or oxetane), ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone), multicyclic forms (e.g., tricyclic), and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with a-L-threo-furanosyl-(3'→2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar.

A backbone modification may include, but is not limited to, 2'-deoxy- or 2'-O-methyl modifications. Exemplary modifications include modifications to the 2' position of a nucleic acid, such as 2'-O-methyl, 2'-halo (e.g., 2'-fluoro, 2'-chloro, 2'-bromo, or 2-iodo), 2'-alkyl (e.g., 2'-methyl, 2'-ethyl, 2'-propyl, 2'-allyl, etc., in which alkyl can be an optionally substituted alkyl, as defined herein), 2'-aryl (e.g., 2'-phenyl, in which aryl can be an optionally substituted aryl, as defined herein), 2'-alkaryl (e.g., 2'-benzyl, in which alkaryl can be an aryl group, as defined herein, attached to the parent molecular group through an alkylene group, in which an alkylene group can be a multivalent (e.g., bivalent, trivalent, tetravalent, etc.) form of an alkyl group, as described herein), 2'-amino (e.g., 2'—$NH_2$, etc., in which amino can be $NR^{N1}R^{N2}$, where each of $R^{N1}$ and $R^{N2}$ is, independently, H, alkyl, or alkaryl, or $R^{N1}$ and $R^{N2}$, taken together with the nitrogen atom to which each are attached, form a heterocyclyl group), 2'-alkoxy (e.g., 2'-O-methoxy, 2'-O-ethoxy, etc., in which alkoxy can be —OR, where R is an optionally substituted alkyl group, as described herein), 2'-alkylamino (e.g., 2'-O-methylamino, 2'-O-ethylamino, etc.), 2'-O-alkylamino (e.g., 2'-O-methylamino, 2'-O-ethylamino, etc., in which alkylamino can be an alkyl group, as defined herein, substituted by an amino group, as defined herein), 2'-azido (in which azido is an —$N_3$ group), 2'-O-cyanoalkyl (e.g., 2'-O-cyanomethyl, etc., in which cyanoalkyl can be an alkyl group, as defined herein, substituted by a cyano group (a —CN group)), 2'-O-alkoxyalkyl (e.g., 2'-O-(2-methoxyethyl), etc., in which alkoxyalkyl can be an alkyl group, as defined herein, which is substituted with an alkoxy group, as defined herein), etc.

A phosphate group modification may include, but is not limited to, phosphorothioate, phosphoroselenates, boranophosphates, boranophosphate esters, hydrogen phosphonates, phosphoramidates, phosphorodiamidates, alkyl or aryl phosphonates, phosphotriesters, phosphorodithioates, bridged phosphoramidates, bridged phosphorothioates, or bridged methylene-phosphonates.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 73%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul S F et al., *J. Mol. Biol.* 1990; 215:403-10; Zhang J et al., *Genome Res.* 1997; 7:649-56) or by using the Gap program (Wisconsin Sequence Analysis Package, Version 8 for Unix, Genetics Computer Group, University Research Park, Madison Wis.), using default settings, which uses the algorithm of Smith T F et al., *Adv. Appl. Math.* 1981; 2(4):482-9.

By "protein," "peptide," or "polypeptide," as used interchangeably, is meant any chain of more than two amino acids, regardless of post-translational modification (e.g., glycosylation or phosphorylation), constituting all or part of a naturally occurring polypeptide or peptide, or constituting a non-naturally occurring polypeptide or peptide, which can include coded amino acids, non-coded amino acids, modified amino acids (e.g., chemically and/or biologically modified amino acids), and/or modified backbones.

The term "fragment" is meant a portion of a nucleic acid or a polypeptide that is at least one nucleotide or one amino acid shorter than the reference sequence. This portion contains, preferably, at least about 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1250, 1500, 1750, 1800 or more nucleotides; or 10, 20, 30, 40, 50, 60, 70, 80, 90, 100, 150, 200, 250, 300, 350, 400, 450, 500, 550, 600, 640 amino acids or more. In another example, any polypeptide fragment can include a stretch of at least about 5 (e.g., about 10, about 20, about 30, about 40, about 50, or about 100) amino acids that are at least about 40% (e.g., about 50%, about 60%, about 70%, about 80%, about 90%, about 95%, about 87%, about 98%, about 99%, or about 100%) identical to any of the sequences described herein can be utilized in accordance with the invention. In certain embodiments, a polypeptide to be utilized in accordance with the invention includes 2, 3, 4, 5, 6, 7, 8, 9, 10, or more mutations (e.g., one or more conservative amino acid substitutions, as described herein). In yet another example, any nucleic acid fragment can include a stretch of at least about 5 (e.g., about 7, about 8, about 10, about 12, about 14, about 18, about 20, about 24, about 28, about 30, or more) nucleotides that are at least about 40% (about 50%, about 60%, about 70%, about 80%, about 90%, about 95%, about 87%, about 98%, about 99%, or about 100%) identical to any of the sequences described herein can be utilized in accordance with the invention.

The term "conservative amino acid substitution" refers to the interchangeability in proteins of amino acid residues having similar side chains (e.g., of similar size, charge, and/or polarity). For example, a group of amino acids having aliphatic side chains consists of glycine (G), alanine (A), valine (V), leucine (L), and isoleucine (I); a group of amino acids having aliphatic-hydroxyl side chains consists of serine (S) and threonine (T); a group of amino acids having amide containing side chains consisting of asparagine (N) and glutamine (Q); a group of amino acids having aromatic side chains consists of phenylalanine (F), tyrosine (Y), and tryptophan (W); a group of amino acids having basic side chains consists of lysine (K), arginine (R), and histidine (H); a group of amino acids having acidic side chains consists of glutamic acid (E) and aspartic acid (D); and a group of amino acids having sulfur containing side chains consist of cysteine (C) and methionine (M). Exemplary conservative amino acid substitution groups are valine-leucine-isoleucine (VLI), phenylalanine-tyrosine (FY), lysine-arginine (KR), alanine-valine (AV), glycine-serine (GS), glutamate-aspartate (ED), and asparagine-glutamine (NQ), as well as any described herein. Accordingly, for any polypeptide sequence described herein, the present invention may also encompass one or more conservative amino acid substitutions.

For a polypeptide sequence described herein, the recited sequence may also encompass a conservative subset, which can include a conservation between groups of strongly similar properties or a conservation between groups of weakly similar properties, as described herein. Exemplary conservative subsets include those having a conservation between groups of strongly similar properties; as well as those having a conservation between groups of weakly similar properties, as known to those of ordinary skill in the art.

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith T F et al., *J. Mol. Biol.* 1981; 147:195-7) and BLAST (Basic Local Alignment Search Tool; Altschul S F et al., *J. Mol. Biol.* 1990; 215:403-10). These and other alignment algorithms are accessible using publicly available computer software such as "Best Fit" (Smith T F et al., *Adv. Appl. Math.* 1981; 2(4):482-9) as incorporated into GeneMatcher Plus™ (Schwarz and Dayhof, "*Atlas of Protein Sequence and Structure*," ed. Dayhoff, M. O., pp. 353-358, 1979), BLAST, BLAST-2, BLAST-P, BLAST-N, BLAST-X, WU-BLAST-2, ALIGN, ALIGN-2, CLUSTAL, CLUSTAL OMEGA, T-COFFEE, MUSCLE, MAFFT, or Megalign (DNASTAR). In addition, those skilled in the art can determine appropriate parameters for measuring alignment, including any algorithms needed to achieve optimal alignment over the length of the sequences being compared. In general, for polypeptides, the length of comparison sequences can be at least five amino acids, preferably 10, 20, 30, 40, 50, 60, 70, 80, 90, 100, 125, 150, 175, 200, 250, 300, 400, 500, 600, 700, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, 1000, 1100, 1200, 1300, 1400, 1500, 1600, 1700, 1800, 1900, 2000, 2100, or more nucleotides, up to the entire length of the nucleic acid molecule. It is understood that for the purposes of determining sequence identity when comparing a DNA sequence to an RNA sequence, a thymine nucleotide is equivalent to an uracil nucleotide.

By "substantial identity" or "substantially identical" is meant a polypeptide or nucleic acid sequence that has the same polypeptide or nucleic acid sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least about 90%, 95%, 96%, 97%, 98%, 99%, or 100% sequence identity to the reference amino acid sequence. For polypeptides, the length of comparison sequences will generally be at least 5,6,7,8,9, 10, 11, 12, 13, 14, 15, 16, 17, 18, 19,20,25,50,75,90, 100, 150, 200, 250, 300, or 350 contiguous amino acids (e.g., a full-length amino acid sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, WI, 53705). Such software may match similar sequences by assigning degrees of homology to various substitutions, deletions, and other modifications. If any conflicting results are obtained for anything recited in the claims appended hereto, the Sequence Analysis Software Package of the Genetics Computer Group, University of Wisconsin Biotechnology Center, 1710 University Avenue, Madison, WI, 53705 should be used.

A "host," as used herein, denotes an in vivo or in vitro eukaryotic cell, a prokaryotic cell (e.g., bacterial or archaeal cell), or a cell from a multicellular organism (e.g., a cell line) cultured as a unicellular entity, which eukaryotic or prokaryotic cells can be, or have been, used as recipients for a nucleic acid, and include the progeny of the original cell which has been transformed by the nucleic acid. It is understood that the progeny of a single cell may not necessarily be completely identical in morphology or in genomic or total DNA complement as the original parent, due to natural, accidental, or deliberate mutation. A "recombinant host" (also referred to as a "genetically modified host cell") is a host cell into which has been introduced a heterologous nucleic acid, e.g., an expression vector. For example, a subject bacterial host cell is a genetically modified bacterial host cell by virtue of introduction into a suitable bacterial host cell of an exogenous nucleic acid (e.g., a plasmid or recombinant expression vector) and a subject eukaryotic host cell is a genetically modified eukaryotic host cell (e.g., a mammalian germ cell), by virtue of introduction into a suitable eukaryotic host cell of an exogenous nucleic acid.

As used herein, the term "exogenous" in reference to a nucleic acid or a polypeptide refers to a nucleic acid or a polypeptide that is not normally or naturally found in and/or produced by a given bacterium, organism, or cell in nature. As used herein, the term "endogenous" in reference to a nucleic acid or a polypeptide refers to a nucleic acid or a polypeptide that is normally found in and/or produced by a given bacterium, organism, or cell in nature.

A "vector" or "expression vector" is a replicon, such as plasmid, phage, virus, or cosmid, to which another nucleic acid segment, i.e., an "insert", may be attached so as to bring about the replication of the attached segment in a cell.

An "expression cassette" comprises a nucleic acid coding sequence operably linked, as defined herein, to a promoter sequence. Exemplary promoter sequences can include a nucleic acid regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation, as well as protein binding domains (consensus sequences) responsible for the binding of RNA polymerase. Eukaryotic promoters will often, but not always, contain "TATA" boxes and "CAT" boxes. Prokaryotic promoters can contain Shine-Dalgarno sequences in addition to the −10 and −35 consensus sequences.

An "expression control sequence" can be a nucleic acid sequence that controls and regulates the transcription and translation of another nucleic acid sequence. A coding sequence is "under the control" of transcriptional and translational control sequences in a cell when RNA polymerase transcribes the coding sequence into mRNA, which is then translated into the protein encoded by the coding sequence. Exemplary transcriptional and translational control sequences are DNA regulatory sequences, such as promoters, enhancers, polyadenylation signals, terminators, and the like, that provide for the expression of a coding sequence in a host cell.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

"Operably linked" or "operatively linked" or "operatively associated with," as used interchangeably, refers to a juxtaposition wherein the components so described are in a relationship permitting them to function in their intended manner. For instance, a promoter is operably linked to a coding sequence if the promoter affects its transcription or expression. A nucleic acid molecule is operatively linked or operably linked to, or operably associated with, an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

In accordance with the present disclosure, there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; *Hames & Higgins eds.*, 1985, "Nucleic Acid Hybridization"; *Hames & Higgins, eds.*, 1984, "Transcription And Translation"; *Freshney, ed.*, 1986, "Animal Cell Culture"; IRL.

By "attaching," "attachment," or related word forms is meant any covalent or non-covalent bonding interaction between two components. Non-covalent bonding interactions include, without limitation, hydrogen bonding, ionic interactions, halogen bonding, electrostatic interactions, $\pi$ bond interactions, hydrophobic interactions, inclusion complexes, clathration, van der Waals interactions, and combinations thereof.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the disclosed technology will be apparent from the following description and the claims.

BRIEF DESCRIPTION OF THE DRAWINGS

FIG. 7 lists SEQ ID NO: 1.

FIG. 8 lists SEQ ID NOs: 2 and 3.

FIG. 9 lists SEQ ID NOs: 4 and 5.

FIG. 10 lists SEQ ID NOs: 6 and 7.

DETAILED DESCRIPTION OF THE INVENTION

The present disclosure relates, in part, to methods and compositions (e.g., engineered hosts) for use in converting xylose-containing lignocellulosic biomass. In particular embodiments, the methods include use of an engineered Rhodosporidium yeast, such as R. toruloides, the engineered R. toruloides having the RT04_9774 Uniprot ID: A0A0K3CLY8 (SEQ ID NO: 1)(FIG. 7) gene deleted from its genome combined with a xylose-containing medium such as a biomass. XylB and XylC are also incorporated into the reaction mixture (or fermentation broth by addition to the R. toruloides genome via *agrobacterium*-mediated transformation).

As a result of employing a high throughput method to probe strain fitness of a barcoded library of Rhodosporidium mutants on various conditions (RB-TDNAseq), as well as looking at enzymology and expression data, it was concluded that RTO4_9774 is the major xylose reductase expressed in R. toruloides. The RB-TDNAseq method is described in more detail by Coradetti, S. T., et al., "*Func-*

*tional genomics of lipid metabolism in the oleaginous yeast Rhodosporidium toruloides,*" eLife 7 (2018) doi:10.7554/ eLife.321 10, incorporated herein by reference. In order to produce xylose-derived bioproducts (e.g., xylonic acid) that directly compete with native metabolism for xylose found in lignocellulosic biomass hydrolysates at high yields, it was determined that native activity in R. toruloides catabolizing xylose toward cellular growth should be diminished or abolished. As disclosed herein, the inventors identified and successfully deleted RT04_9774 from the R. toruloides genome. Although minimal growth on xylose-containing medium still occurs with this engineered R. toruloides, it is at a much slower pace compared to wild type.

This gene-deletion strain was integrated with a two-step pathway, by addition of XylB and XylC, thereby converting d-xylose into xylonic acid from *Caulobacter* vibriodes CB15. After medium optimization, near theoretical maximum production of xylonic acid from xylose was obtained.

Data indicates that RT04_9774 is the first step in xylose metabolism in R. toruloides. It was determined that RT04_9774 is likely the major xylose reductase gene acting in R. toruloides based on several pieces of information. Under xylose conditions, RT04_9774 is highly upregulated (more than other putative xylose reductases RT04_13562 and RT04_11882) and RT04_9774 has some sequence similarity to known xylose reductases. Additionally, it has been reported that the purified enzyme has dehydrogenase activity on xylose, arabinose, glyceraldehyde and other carbon sources (Protzko et al. 2019). Lastly, as shown herein, deletion of RT04_9774 was confirmed to slow growth on xylose considerably.

Figure 1:
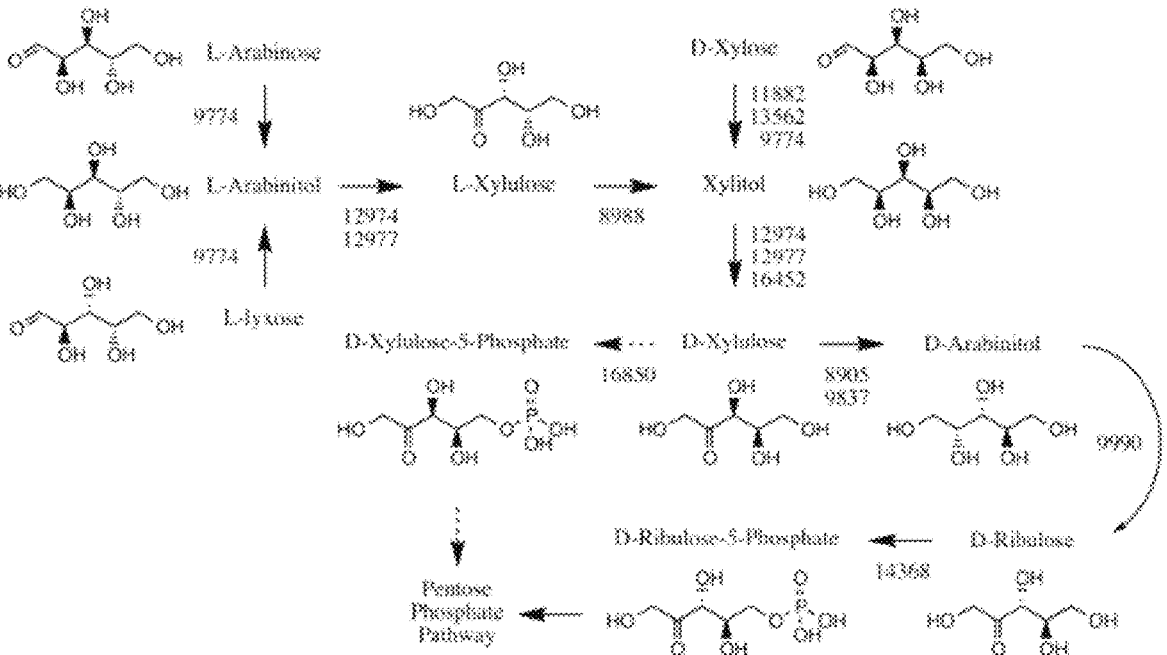
FIG. 1 is reaction scheme showing a pentose utilization pathway in R. toruloides in contact with a xylose-containing source.

FIG. 1 discloses a pentose utilization pathway in R. toruloides in contact with a xylose-containing source. Pentose sugars and alcohols are converted to D-ribulose-5-phosphate via D-arabinitol dehydrogenases before entering the pentose phosphate pathway.

Figure 2:
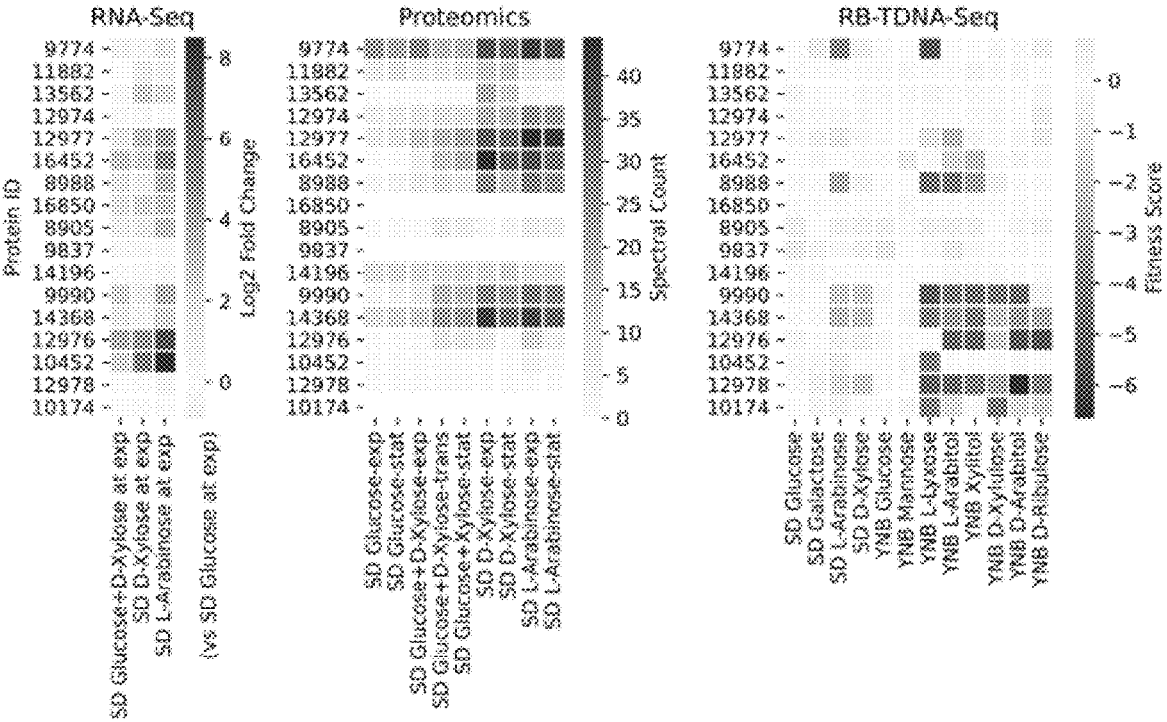
FIG. 2 is a series of graphs showing gene expression, protein expression, and fitness scores for pentose utilization pathway genes.

FIG. 2 shows gene expression, protein expression, and fitness scores for pentose utilization pathway genes (exp means exponential phase; trans means transition phase; stat means stationary phase) (Kim, J., et al., "Multi-Omics Driven Metabolic Network Reconstruction and Analysis of Lignocellulosic Carbon Utilization in Rhodosporidium toruloides," Front. Bioeng. *Biotechnol.* 8, 612832. (2020) doi: 10.3389/fbioe.2020.612832). The darker areas indicate more relative transcripts vs the control or reference condition (i.e., for RNA-seq), more absolute peptide counts (i.e., for proteomics), and lesser growth/lower fitness score relative to the time-zero population (i.e., for RB-TDNA-seq) for the experimental conditions listed at the bottom of the three graphs. The protein IDs on the left of the graphs correspond to the same numbers listed in the reaction pathway shown in FIG. 1.

Thus, deletion of the RT04_9774 gene was attempted and successfully completed. The engineered R. toruloides dramatically slowed the pathway to xylose conversion to biomass compared to wild type R. toruloides. While glucose continued to be processed as normal to be converted to biomass, a large percentage of xylose was converted to xylonic acid.

Figure 3:
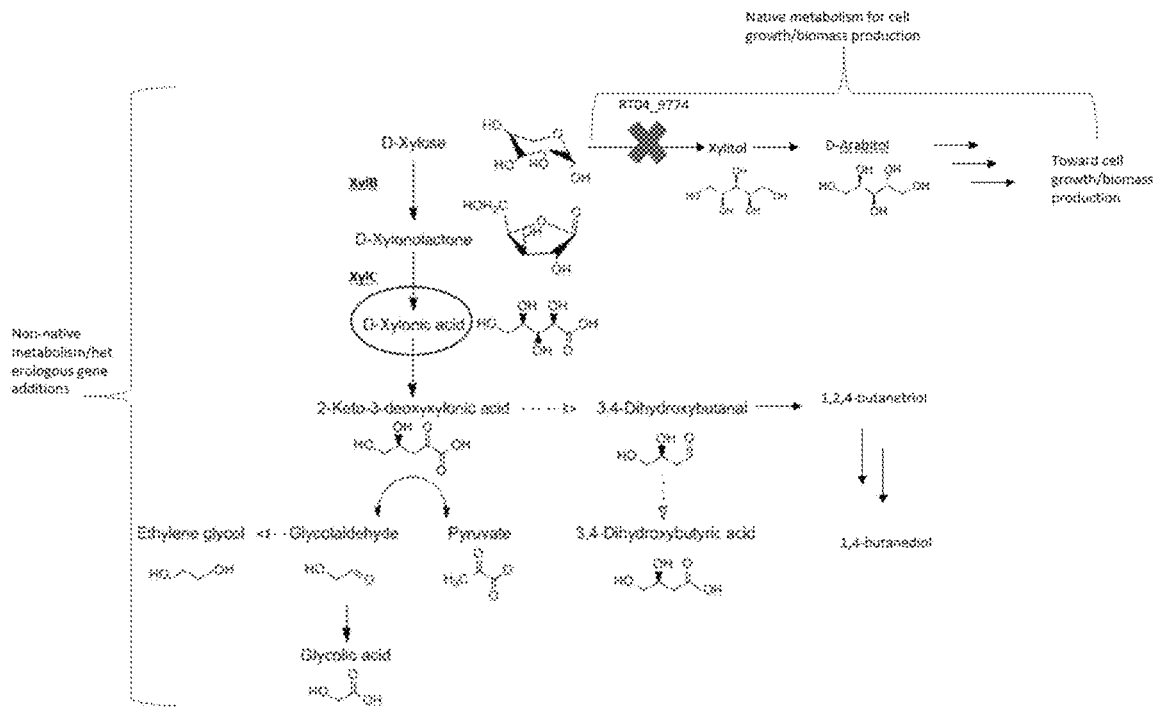
FIG. 3 is a reaction scheme showing the native metabolic pathway for R. toruloides and the non-native metabolic pathway that is believed to take place when the RT04_9774 gene is deleted from R. toruloides with the addition of heterologous genes.

FIG. 3 shows the native metabolic pathway for R. toruloides and the non-native metabolic pathway that is believed to take place when the RT04_9774 gene is deleted from R. toruloides. The non-native metabolic pathway is aided by heterologous gene additions of XylB and XylC. XylB converts D-xylose to D-xylono-1,5-→lactone, and XylC converts D-xylono-1,5-lactone to D-Xylonic acid. Depending on pH, xylonate may be present as well (as determined by its pKa). Depicted is the modified xylose pathway of pGAPDH-XylB pTEF1-XylC (i.e., RT04_9774 deletion strain with strong native promoters, pGAPDH and pTEF1 (SEQ ID NO: 6 and 7, respectively, disclosed in FIG. 10), driving high expression of XylB and XylC). It was determined that in order to produce xylonic acid at high yields, the first step of xylose conversion to biomass (i.e., through RT04_9774) should be removed or suppressed. It was determined that deleting the RT04_9774 gene would accomplish that purpose.

As shown in FIG. 3, other bioproducts of interest can be ultimately derived from xylose via the new pathway to xylonic acid.

Engineered microbial hosts disclosed herein can be derived from a Eukaryote microorganism, including yeast, such as a Basidiomycete yeast. The terms "cell," "microbial cells," and "microbes" are used interchangeably with the term microorganism. The term "host" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

In an embodiment, the microbial host is a Rhodosporidium microorganism. It has been reported that these yeast cells are globose, ovoid, or elongate, and that budding is multilateral or polar. Ballistoconidia do not form. Carotenoid pigments are visible and the cultures are pink to orange in color. Some species are heterothallic, and others are self-fertile. See Jos6 Paulo Sampaio, in "The Yeasts" (Fifth Edition), 2011 (publisher summary).

The genus Rhodosporidium includes, for example, R. toruloides, R. azoricum, R. fluviale, R. *lusitaniae*, R. babjevae, R. diobovatumn., R. paludigenun, R. *sphaerocarpum*. and R. krawochvilovae. Such hosts can be transformed to provide an engineered host. R. toruloides, in particular, is an attractive host, as it is compatible with many hydrolysates (i.e., tolerant to various biomass hydrolysate inhibitors), has naturally high concentration of AcCoA used to form lipid droplets (i.e., TAGs) as a form of energy storage that can be exploited for fatty acid-like products and terpenes. Tends to grow well over a wide range medium pHs, is genetically tractable, can consume a wide variety of carbon sources, including p-coumarate from lignin degradation present is biomass hydrolysates.

In an embodiment, the engineered host can be derived from any Basidiomycete organism so long as the Basidiomycete has a gene with 70% or greater sequence identity to RT04_9774 in its genome, such as, for example, 73% or greater, 80% or greater, 90% or greater, or 98% or greater sequence identity to RT04_9774 in its genome. Being "derived from" in this context means that the organism is subjected to the gene deletion described herein. The engineered host has the gene with 80% or greater, 90% or greater, 95% or greater, or 98% or greater sequence identity to the RT04_9774 gene deleted from its genome. The base Basidiomycete organism from which the engineered organism is derived can be selected from Rhodosporodium and any members thereof that contain the gene with 70% or greater sequence identity to RT04_9774 gene, such as, for example, 73% or greater, 80% or greater, 90% or greater, or 98% or greater sequence identity to RT04_9774 in its genome.

Exemplary methods of engineering of the base organism include, for example, gene deletion or heterologous gene integration via lithium acetate or CRISPR-Cas9-mediated transformations (Otoupal, P. B., et al., "Multiplexed CRISPR-Cas9-Based Genome Editing of Rhodosporidium toruloides," *MSphere* 4 (2019) incorporated herein by reference), or AtMT (Zhuang, X., et al. "Monoterpene production by the carotenogenic yeast Rhodosporidium toruloides," *Microb. Cell Fact.* 18, 54 (2019) incorporated herein by reference.)

Exemplary sources of xylose include a lignocellulosic xylose-containing material, such as are found in various biomass or biomass-derived materials. The lignin of the lignocellulosic material may, e.g., be formed from a combination of one or more monomers, such as a monolignol monomer, a p-coumaryl alcohol or an alkoxyl form thereof (e.g., a methoxylated form, including mono- and di-methoxylated forms), a coniferyl alcohol or an alkoxyl form thereof (e.g., a methoxylated form), a coumaryl alcohol of an alkoxyl form thereof (e.g., a methoxylated form), and a sinapyl alcohol or an alkoxyl form thereof (e.g., a methoxylated form). In other embodiments, lignin or a lignin derivative can be characterized by the presence of one or more aromatic functional groups, such as a p-hydroxyphenyl group, a guaiacyl group, and/or a syringyl group.

Lignin can have different compositions depending on the plant material from which the lignin is derived. Exemplary lignin can include softwood lignin (e.g., derived from softwood and including of from about 25% to about 30% (w/w) of lignin), compression wood lignin (e.g., derived from compression wood and including of from about 35% to about 40% (w/w) of lignin), typical hardwood lignin (e.g., derived from hardwood and including of from about 20% to about 25% (w/w) of lignin), tropical hardwood lignin (e.g., derived from tropical hardwood and including of from about 30% to about 40% (w/w) of lignin), tension wood lignin (e.g., derived from tension wood and including of from about 20% to about 25% (w/w) of lignin), wheat lignin (e.g., derived from wheat, including any useful part of plant, such as the root, leaves, shoots, and/or stems), maize lignin (e.g., derived from maize, including any useful part of plant, such as the root, leaves, shoots, and/or stems; and including of from about 20% to 75% (w/w) of lignin), mixed grasses lignin (e.g., derived from mixed grasses, including any useful part of plant, such as the root, leaves, shoots, and/or stems).

The xylose-containing source can include various monosaccharides other than xylose, such as, e.g., pectin-derived monosaccharides, dextrose, fructose, galactose, glucose, or maltose, oligosaccharides, polysaccharides (e.g., cellulose, hemicellulose, or starch), cellulosic material, fatty acids (e.g., saturated or unsaturated fatty acids), biomass hydrolysates, metabolic intermediates (e.g., acetate, lactate, or succinate), alcohols and sugar alcohols (e.g., ethanol, ethylene glycol, glycerol, inositol, malitol, mannitol, sorbitol, or xylitol), lignin and lignin compounds (as discussed above), plants and plant products (e.g., corn, liquefied corn meal, corn steep liquor (a byproduct of corn wet milling process that contains nutrients leached out of corn during soaking), corn stover, corn fiber, rice straw, woody plants, herbaceous plants, molasses, etc., which can be found in, for example, in the stems, leaves, hulls, husks, and cobs of plants; or in the leaves, branches, and wood of trees), herbaceous material, agricultural residues, forestry residues, municipal solid wastes, waste paper, as well as pulp and paper mill residues, or mixtures thereof.

In an embodiment, the two enzymes XylB (from *Caulobacter* vibrioides CB15 encoding D-xylose dehydrogenase) and/or XylC (from *Caulobacter* vibrioides CB15 encoding D-xylono-1,5-lacoine lactonasc) are introduced and incorporated into the fermentation strain. These can be incorporated at the same time or in a step-wise manner. These enzymes induce xylose catabolism in the process. Sequences for the unoptimized (i.e., native *Caulobacter* vibrioides CB15 sequences) XylB and XylC are disclosed in FIG. 8 as SEQ ID NOs: 2 and 3, respectively.

After successful deletion of RT04_9774 from the yeast to make an engineered host, codon-optimized sequences of XylB (Uniprot ID: Q9A9Z0) and XylC (Uniprot ID: Q9A9Z1) from the bacterium *Caulobacter* vibrioides CB15 were integrated onto the R. toruloides genome via *agrobacterium*-mediated transformation (i.e., randomly inserted throughout the genome with varying copy number. This can be performed as described in in Zhuang, X., et al., "Monoterpene production by the carotenogenic yeast Rhodosporidium toruloides," *Microb. Cell Fact.* 18, 54 (2019) incorporated herein by reference).

After integration of heterologous XylB and XylC into R. toruloides, individual transformants were screened for xylonic acid titers in a lignocellulosic hydrolysate described in Chen, et al., "DMR (deacetylation and mechanical refining) processing of corn stover achieves high monomeric sugar concentrations (230 g $L^{-1}$) during enzymatic hydrolysis and high ethanol concentrations (>10% v/v) during fermentation without hydrolysate purification or concentration," *Energy Environ. Sci.* 9, 1237-1245 (2016). doi: 10.1039/C5EE03718B.

In an embodiment, the xylose-derived product, xylonic acid or xylonate, may be excreted from R. toruloides into the hydrolysate supernatant and was measured by HPLC using a BioRad Aminex 87-C column at 0.6 mL/min with water as the eluant and quantified with a refractive index detector with peak areas converted to concentrations using an external standard curve of known xylonate concentrations.

In an embodiment, large scale processing can involve vessels on the order or thousands of liters and will utilize a method of cell separation coupled to purification and crystallization of xylonate by means of ion-exchange resins, activated charcoal, pH adjustment, chromatographic fractionation, liquid-liquid extraction, precipitation, or a combination thereof.

In an embodiment, the fermentation broth has a pH of 2 to 7.5, such as about 5 to about 7, or about 5.5 to about 6. Buffers may be added to the broth to maintain the pH in these ranges. It was determined that the engineered organism works best in these ranges.

In accordance with methods disclosed herein, yields were obtained near theoretical yield levels, such as 80% to 99%, 85% to 98%, or 90% to 96% by weight of theoretical yield of xylonic acid, xylonate, or a combination of these.

In an embodiment, to further optimize the process and materials for increasing yield of the xylose derived product, additional steps can be taken. For example, the XylB and XylC enzymes can be codon optimized for the engineered host. The sequences for codon-optimized XylB and XylC are disclosed in FIG. 9 as SEQ ID NOS. 4 and 5, respectively. Codon optimization was performed using a R. toruloides-specific codon usage table that tallied the frequency of codon usage for all protein-encoding sequences in the genome. Using this table, XylB and XylC were codon optimized by choosing the most frequently used codons for each of the amino acids present in XylB and XylC.

In an embodiment, the biomass hydrolysate is nitrogen deficient and is supplemented with a nitrogen source. Two sources, for example, urea and ammonium sulfate are used in culturing the R. toruloides and, upon assimilation, the pH typically increases and decreases, respectively. Therefore, when producing an acidic product (e.g., xylonic acid), addition of urea to the biomass hydrolysate provides the nitrogen while also acting as a buffer to the acidic product. This increases yields because the fermentation is able to reach complete sugar utilization within growth-permitting pH range. Similar results can likely be achieved by addition of another base coupled with a pH-neutral nitrogen source such as yeast extract. Such nitrogen sources coupled with buffers or other pH control mechanism should reach relatively high titers.

EXAMPLES

Example 1: Xylose-Containing Source Material

Corn stover (INL LOT #6) from Hurley County, South Dakota was processed by the method disclosed in Chen, et al., "DMR (deacetylation and mechanical refining) processing of corn stover achieves high monomeric sugar concentrations (230 g $L^1$) during enzymatic hydrolysis and high ethanol concentrations (>10% v/v) during fermentation without hydrolysate purification or concentration," *Energy Environ. Sci.* 9, 1237-1245 (2016). doi:10.1039/C5EE03718B, incorporated herein by reference. This resulted in deacetylated mechanically refined corn stover hydrolysate starting material with a high monomeric sugar concentration: 160 g/L glucose and 80 g/L xylose.

Example 2: Engineered Host

Rhodosporidium toruloides strain IFO 0880 (a.k.a. NBRC 0880) was obtained from the Biological Resource Center, NITE (NBRC), Japan. An R. toruloides was engineered to remove the RT04_9774 gene by homologous recombination (i.e., full deletion mutant) achieved by transforming R. toruloides with linearized DNA by a lithium acetate transformation protocol as described in (Otoupal et al., 2019). The linearized DNA was composed of a gene sequence encoding resistance to a fungal antibiotic, G418, flanked by 45 bp homology arms to RT04_9774. DNA oligos used to create this linear DNA fragment were:

| (SEQ ID NO: 8) 9774.LHF.F | 5'-CCCGCTCGCTCGCTGAAAAAGTGCGCTGGGGCTG CTTGATCGATG tcgctcgtcttgttt-3' |
|---|---|
| (SEQ ID NO: 9) 9774.RHF.R | 5'-TCTCGACGGGCCTCTCCTCGCTCTCACGTCTCCC AAACTCGCCCA gagccgacggagaac-3' |

After integration of the linear DNA, transformants were screened for the deletion of RT04_9774 using primers:

| (SEQ ID NO: 10) LHF.162B.F2 | 5' TGAGCGTGTCGAGCTTCGCGACGTTCGGTA 3' |
|---|---|
| (SEQ ID NO: 11) LHF.162B.R2 | 5' AGCGGGTCAGTGAGCGGGTCTGGTGGG 3' |
| (SEQ ID NO: 12) LHF2.162B.R2 | 5' tcgcgcgcccacttgtagccgtagaggtc 3' |

The engineered R. toruloides with RT04_9774 gene deletion was further modified with R. toruloides native promoters for expressing XylB and XylC, pGAPDH-XylB and pTEF1-XylC (SEQ ID NOs: 4 and 5) (i.e., engineered strain with strong native promoters, pGAPDH & pTEF1 (SEQ ID NOs: 6 and 7), driving high expression of XylB and XylC) and was then grown in batch cultures of DMR biomass hydrolysate (i.e., corn stover hydrolysate) of Example 1.

Example 3: Experiments with Engineered Host and Xylose-containing Source Material and Comparisons A comparison test of the engineered host of Example 2 versus the wild-type R. toruloides was performed by comparing the growth of wild-type R. toruloides versus Example 2 on xylose minimal medium.

The full recipe for the xylonate titers presented here was:
DMR hydrolysate (~160 g/L glucose+~80 g/L xylose)
9 g/L urea
100 µM FeSO4
400 µg/L thiamine hydrochloride
400 µg/L pyridoxine hydrochloride
1 mM Na$_2$SO$_4$
120 mM KH$_2$PO$_4$
80 mM K$_2$HPO$_4$;
final medium pH ~6

Figure 4:
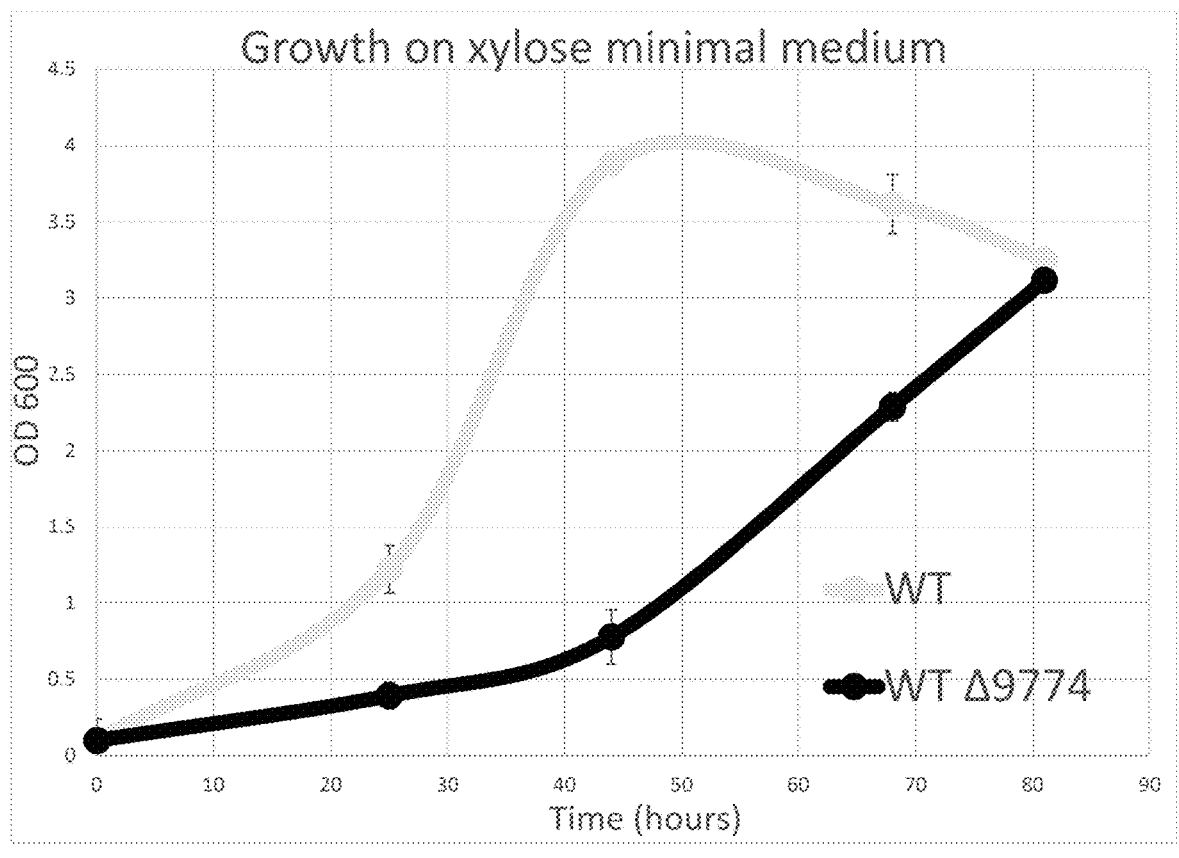
FIG. 4 is a graph showing a growth experiment of wild-type R. toruloides versus the engineered host.

FIG. 4 shows the growth over time. OD 600 is a measure of biomass concentration via absorbance of light at 600 nm. (The engineered host of Example 2 is denoted as KO 9774 on FIG. 4.)

Figure 5:
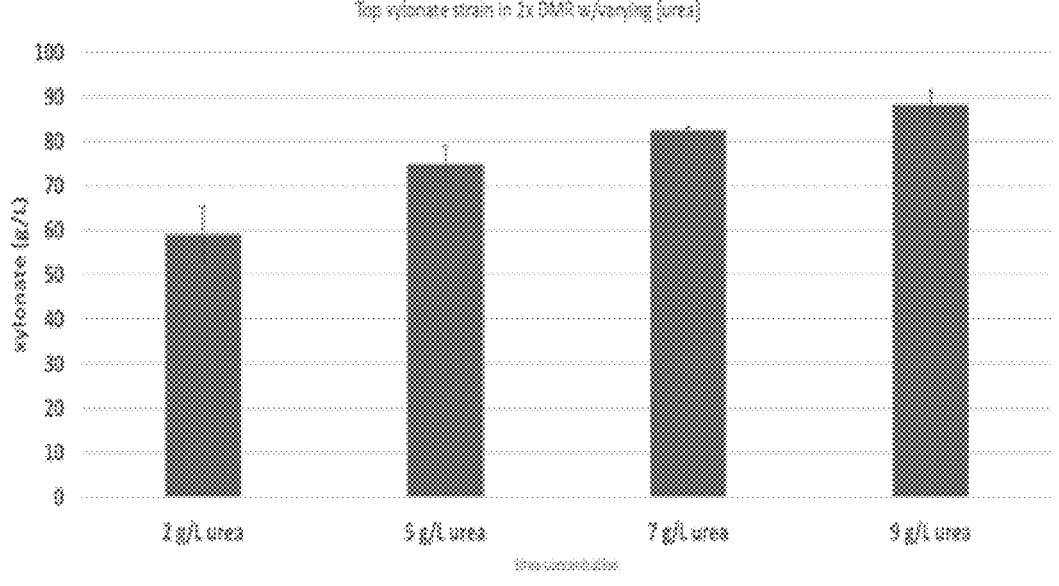
FIG. 5 is a graph showing the effect of addition of urea to DMR to improve xylonic acid titers.

After some minor medium optimization, including switching the nitrogen source from ammonium sulfate to urea, titers of ~86 g/L xylonic acid were achieved at ~96% of the maximum theoretical yield from xylose present in the DMR source. When producing an acidic product (e.g., xylonic acid), addition of urea to biomass hydrolysate provides the necessary nitrogen while also acting as a buffer to the acidic product. This increases yields because the fermentation is able to reach complete sugar utilization within growth-permitting pH range. FIG. 5 shows the effect of addition of urea to DMR to improve xylonic acid titers.

Figure 6:
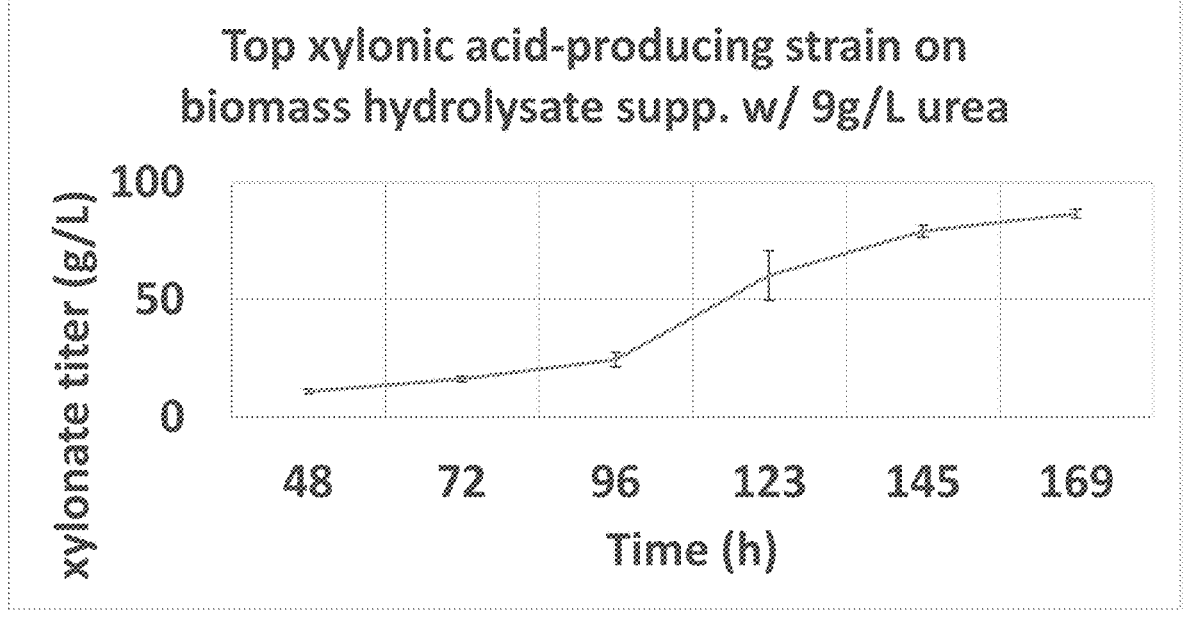
FIG. 6 is a graph showing xylonate titers over time as described in Example 3.

Finally, FIG. 6 shows the productivity of a top xylonic acid-producing strain of Example 2 on the DMR source of Example 1. Again, the engineered host here is the R. toruloides with 9774 deleted gene from Example 2. Samples were taken periodically throughout the culture to measure increasing xylonate titers. R. toruloides undergoes diauxic growth, preferentially consuming glucose first, then xylose. This is reflected in FIG. 6 with low rates of xylonate productivity until 96h (while mainly glucose is consumed), followed by a sharp increase in productivity>96h (while mainly xylose is consumed). Since only xylose can be converted to xylonate, FIG. 6 indicates that glucose in the culture is converted solely to biomass for approximately the first 96h, and after 96 h, the same biomass in the culture converts nearly all the xylose to xylonate or xylonic acid.

All publications, patents, patent applications, and accession no. entries mentioned in this specification are incorporated herein by reference to the same extent as if each independent publication or patent application was specifically and individually indicated to be incorporated by reference.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim. The term "consisting essentially" as used herein means the specified materials or steps and those that do not materially affect the basic and novel characteristics of the material or method. Unless the context indicates otherwise, all percentages and averages are by weight. If not specified above, the properties mentioned herein may be determined by applicable ASTM standards, or if an ASTM standard does not exist for the property, the most commonly used standard known by those of skill in the art may be used. The articles "a", "an", and "the" should be interpreted to mean "one or more" unless the context indicates the contrary.

---

It is claimed:

1. An engineered organism comprising an engineered host derived from a Basidiomycete organism having a gene with at least 95% sequence identity to SEQ ID NO: 1 in its genome, the engineered host having the gene with 95% or greater sequence identity to SEQ ID NO: 1 deleted from its genome;

wherein XylB and XylC are expressed in the engineered host; and the engineered organism is capable of producing xylonic acid, xylonate, or a combination thereof.

2. The engineered organism of claim 1, wherein the engineered host is Rhodosporidium having the gene with 95% or greater sequence identity to SEQ ID NO: 1 deleted from its genome.

3. The engineered organism of claim 2, wherein the engineered host is R, toruloides with the gene with at least 99% sequence identity to SEQ ID NO: 1 deleted from its genome.

4. The engineered organism of claim 1, wherein XylB and XylC are codon optimized for the engineered host.

5. A fermentation broth composition, comprising an energy source comprising xylose and an engineered host, the engineered host being derived from a Basidiomycete organism having a gene with at least 95% sequence identity to SEQ ID A NO: 1 in its genome, and the engineered host having the gene with at least 95% sequence identity to SEQ ID NO: 1 deleted from its genome;

wherein XylB and XylC are expressed in the engineered host; and the fermentation is capable of producing xylonate, or a combination thereof.

6. The fermentation broth composition of claim 5, wherein the engineered host is Rhodosporidium having the gene with at least 95% sequence identity to SEQ ID NO: 1 deleted from its genome.

7. The fermentation broth composition of claim 6, wherein the engineered host is R, toruloides having the gene with at least 95% sequence identity to SEQ ID NO: 1 deleted from its genome.

8. The fermentation broth composition of claim 5, wherein the fermentation broth composition has a pH of about 5.5 to about 6.

9. The fermentation broth composition of claim 5, wherein the energy source is a biomass hydrolysate.

10. The fermentation broth composition of claim 5, wherein gene sequences XylB and XylC are codon optimized for the engineered host.

11. The fermentation broth composition of claim 5, wherein the energy source is a corn stover hydrolysate.

12. A method of making a xylose-derived product via a fermentation broth, comprising:

expressing XylB and XylC in the fermentation broth via introducing promoter sequences for expressing XylB and XylC in an engineered host:

combining an energy source comprising xylose and the engineered host, the engineered host being derived from a Basidiomycete organism having a gene with at least A 95% sequence identity to SEQ ID NO: 1 in its genome, and the engineered host A having the gene with at least 95% sequence identity to SEQ ID NO: 1 deleted from its genome; and the method produces xylonic acid, xylonate, or a combination thereof.

13. The method of claim 12, wherein the energy source is a biomass hydrolysate.

14. The method of claim 12, wherein the energy source is deacetylated mechanically refined corn stover.

15. The method of claim 12, wherein the engineered host is derived from Rhodosporidium.

16. The method of claim 12, wherein the engineered host is R, toruloides having SEQ ID NO: 1 deleted from its genome.

17. The method of claim 12, further comprising adding a nitrogen source to the fermentation broth.

18. The method of claim 12, wherein the fermentation broth has a pH of about 5.5 to about 6.

19. The method of claim 12, wherein the method yields 80% to 99% by weight of theoretical yield of xylonic acid, xylonate, or a combination thereof.

20. The method of claim 12, wherein XylB and XylC are codon optimized for the engineered host.

\* \* \* \* \*